(12) United States Patent
Tsukada (10) Patent No.: US 8,608,927 B2
(45) Date of Patent: Dec. 17, 2013

(54) ION SENSOR

(75) Inventor: Keiji Tsukada, Okayama (JP)

(73) Assignee: National University Corporation Okayama University, Okayama (JP)

( * ) Notice: Subject to any disclaimer, the term of this patent is extended or adjusted under 35 U.S.C. 154(b) by 328 days.

(21) Appl. No.: 13/145,943

(22) PCT Filed: Jan. 28, 2010

(86) PCT No.: PCT/JP2010/051087
§ 371 (c)(1),
(2), (4) Date: Jul. 22, 2011

(87) PCT Pub. No.: WO2010/087383
PCT Pub. Date: Aug. 5, 2010

(65) Prior Publication Data
US 2011/0272280 A1    Nov. 10, 2011

(30) Foreign Application Priority Data

Jan. 30, 2009    (JP) ................................. 2009-019940

(51) Int. Cl.
*G01N 27/333* (2006.01)
(52) U.S. Cl.
USPC .......................................... 204/416; 204/433
(58) Field of Classification Search
USPC ............... 204/416–419, 433; 205/787.5, 789, 205/789.5
See application file for complete search history.

(56) References Cited

FOREIGN PATENT DOCUMENTS

| JP | 07-035747 | | 2/1995 | |
|----|-----------|---|--------|---|
| JP | 09-096620 | | 4/1997 | |
| JP | 10-104199 | A * | 4/1998 | ............ G01N 27/46 |
| JP | S63-156065 | U | 10/1998 | |
| JP | 2008-145123 | | 6/2008 | |

OTHER PUBLICATIONS

JPO computer-generated English translation of Kanamaru JP 10-104199 A, patent published Apr. 24, 1998, transalation Aug. 12, 2013.*

(Continued)

*Primary Examiner* — Alex Noguerola
(74) *Attorney, Agent, or Firm* — Sterne, Kessler, Goldstein & Fox, P.L.L.C.

(57) ABSTRACT

Provided is an ion sensor with which the concentration of ions in a solution can be determined without any reference electrode. The ion sensor is equipped with: a first electrode plate; a second electrode plate which has been disposed opposite the first electrode plate and has one or multiple openings; an ion-sensitive film continuously formed so that the film is interposed between the first electrode plate and the second electrode plate, blocks up one side of each opening of the second electrode plate, and extends from the end of that side of the opening to the outer surface of the second electrode plate through the inner wall surface of the opening; and a sensor support which supports the second electrode plate so that when the ion concentration of a test solution to be examined is determined, the ion-sensitive film comes into contact with the test solution only in the portions thereof that have been formed in each opening and on the outer surface of the second electrode plate. The ion sensor is configured so that the thickness of the ion-sensitive film interposed between the first electrode plate and the second electrode plate is different from the thickness of the ion-sensitive film formed on the outer surface of the second electrode plate. A difference in potential between the first electrode plate and the second electrode plate is measured.

8 Claims, 8 Drawing Sheets

(56) References Cited

OTHER PUBLICATIONS

JPO computer-generated English translation of Hayashi JP 09-96620 A, patent published Apr. 8, 1998, translation Aug. 12, 2013.*
International Search Report for International Application No. PCT/JP2010/051087 mailed Apr. 6, 2010, 4 pages.
Desmond, D., et al. "Evaluation of Miniaturised Solid State Reference Electrodes on a Silicon Based Component," *Sensors and Actuators*, B 44 (1997) 389-396.
Bobacka, J., "Conducting Polymer-Based Solid-State Ion-Selective Electrodes," *Electroanalysis* 18, 2006, No. 1, 7-18.
Tsukada, K., et al, "Long-Life Multiple-ISFETs With Polymeric Gates," *Sensors and Actuators*, 18 (1989) 329-336.
Cattrall, R.W., et al., "Coated Wire Ion-Selective Electodes," *Analytical Chemistry*, 1971, 43 (13), 1905-1906.
Bakker, E., et al., "Electrochemical Sensors," *Analytical Chemistry*, 2006, 78 (12), 3965-3984.

* cited by examiner

ION SENSOR

TECHNICAL FIELD

The present invention relates to an ion sensor measuring ion concentration in a solution.

BACKGROUND ART

As an ion sensor measuring ion concentration in a solution, an ion selective electrode is given, and is important and known widely in the field of electrochemistry. From the beginning of the 20th century, a pH electrode in which glass is employed as a pH sensitive film has been known, and is used widely presently. A liquid film type ion selective electrode in which an ion sensitive matter is dispersed with a polymer such as PVC (polyvinyl chloride) and a plasticizer has been used from the 1960s. The ion selective electrode is used as a sensor measuring ion concentration of $K^+$, $Na^+$ and the like in blood in a an analytical instrument for clinical examinations. The ion sensor has been reported by many literatures (see Non-patent Literature 1).

Figure 10:
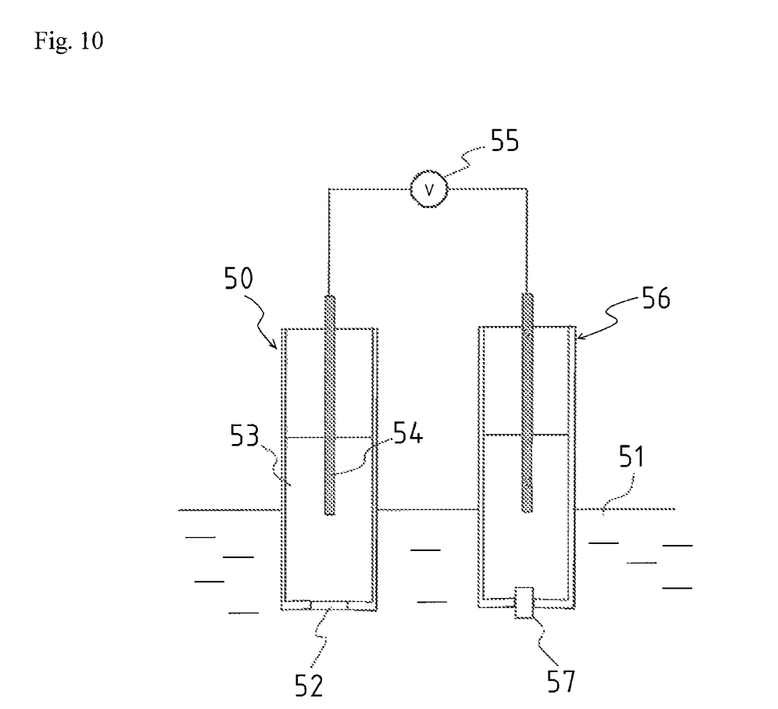
FIG. 10 It is a schematic cross-sectional view of a conventional ion sensor.

As shown in FIG. 10, an ion selective electrode 50 comes into contact with a test solution 51 to be examined through an ion-sensitive film 52, and an internal solution 53 as a standard and an electrode 54 are provided in the ion selective electrode 50. As an internal electrode, an Ag/AgCl electrode is employed.

A coated wire was reported as an ion selective electrode in which an ion-sensitive film is directly formed on an Ag/AgCl electrode without any internal solution (see Non-patent Literature 2).

There is dry chemistry in which all internal solution is solidified and formed sheet-like. For example, Fuji DRI-CHEM of Fujifilm Corporation (DRI-CHEM is a trademark) was reported (see Patent Literature 1).

There have been many trials for miniaturizing an ion sensor, and an ISFET ion-sensitive field effect transistor) was reported in which an ion-sensitive film is formed on a gate of a FET (field-effect transistor). Accordingly, a multi sensor in which various kinds of ion-sensitive films are integrated to one sensor substrate so as to measure various ions simultaneously has been reported (see Non-patent Literature 3).

Especially in recent, for easing instability of a complete individual ion sensor such as the coated wire, various ion sensors in which conductive polymer films are compounded with ion-sensitive films have been reported (Non-patent Literature 4). The ion sensor exchanges ions for electrons between an electrode material and the ion-sensitive film and is reported to be effective for stabilizing the potential in the long run. As the conductive polymer film, polypyrrole, polythiophene, polyaniline, poly(3,4-ethylenedioxythiophene): PEDOT, poly(3-octylthiophene):POT and the like are known, and the conductive polymer film stabilizes the contact potential with the electrode material such as silver, gold, platinum and glassy carbon. In this case, as a method for using the conductive polymer film, the method that the conductive polymer film is formed between the electrode material and the ion-sensitive film and the method that the conductive polymer film is mixed with the ion-sensitive film are given.

Such an ion sensor measures the potential of the ion-sensitive film which is changed corresponding to the concentration of ion to be measured in the solution. The standard potential must be required for measuring the potential, and a reference electrode 56 is employed which is connected through a potentiometer 55 as shown in FIG. 10. Therefore, for miniaturizing the ion sensor, there is a problem of miniaturization of the reference electrode, and several arts for miniaturizing the reference electrode have been reported (see Non-patent Literature 5).

PRIOR PUBLICATION

Patent Literature

Patent Literature 1: the Japanese Patent Laid Open Gazette Hei. 7-35747

Non-patent Literature

Non-patent Literature 1: "Electrochemical Sensors" Eric Bakker and Yu Qin, Anal. Chem. Vol. 78 (2006) pp. 3965-3983

Non-patent Literature 2: "Coated wire ion-selective electrodes" R. W. Cattrall and H. Freiser, Anal. Chem., Vol. 43 (1971) pp. 1905-1906

Non-patent Literature 3: "Long-life multiple-ISFETs with polymeric gates" K. Tsukada, M. Sebata, Y. Miyahara, and H. Miyagi, Sensors and Actuators, Vol. 18 (1989) pp. 329-336

Non-patent Literature 4: "Conducting Polymer-Based Solid-State Ion-Selective Electrodes" Johan Bobacka, Electroanalysis, Vol. 18 (2006) pp. 7-18

Non-patent Literature 5: "Evaluation of miniaturized solid state reference electrodes on a silicon based component" D. Desmond, et. al., Sensors and Actuators, B44 (1997) pp. 389-396

DISCLOSURE OF INVENTION

Problems to be Solved by the Invention

As mentioned above, for miniaturizing the ion sensor, it is necessary to miniaturize the reference electrode. However, an electrode used as the reference electrode with high reliability presently has an Ag/AgCl electrode as an internal electrode and has construction of liquid junction connection with porous ceramic 57 (see FIG. 10) and pin holes for ion exchange of very small amount between the solution to be measured and the internal solution of the reference electrode. Accordingly, the reference electrode must have construction for holding the internal solution, whereby the miniaturization of the liquid junction connection with polymeric material, MEMS structure or the like is employed.

However, actually, there is no reference electrode having internal solution as mentioned above with reliability, and the structure is difficult to be mass-produced. Therefore, there is a problem that the whole including the ion sensor and the reference electrode cannot be miniaturized.

Then, the purpose of the present invention is to provide an ion sensor which does not require any reference electrode and internal solution and can be miniaturized.

Means for Solving the Problems

The present invention is an ion sensor including
a first electrode plate,
a second electrode plate arranged oppositely to the first electrode plate and having one or a plurality of openings,
an ion-sensitive film interposed between the first electrode plate and the second electrode plate, blocking up one of sides of the opening of the second electrode plate, and formed continuously from the end of the side of the opening through the inner wall surface of the opening to the outer surface of the second electrode plate, and a sensor support supporting the second electrode plate so that only the ion-sensitive film formed in the opening and on the outer surface of the second electrode plate comes into contact with a test solution at the time of measuring the test solution.

Difference in potential between the first electrode plate and the second electrode plate is measured while the thickness of the ion-sensitive film interposed between the first electrode plate and the second electrode plate is different from the thickness of the ion-sensitive film formed on the outer surface of the second electrode plate.

The present invention is the ion sensor in which the total area of the one or the plurality of the openings of the second electrode is not less than the half of the area of the part of the first electrode plate facing the second electrode plate.

The present invention is the ion sensor in which the thickness of the ion-sensitive film interposed between the first electrode plate and the second electrode plate is at least not less than the twice of the thickness of the ion-sensitive film formed on the outer surface of the second electrode plate.

The present invention is the ion sensor in which the plurality of the ion sensors mentioned above are disposed on a common sensor support, and the second electrode plates respectively provided in the plurality of the ion sensors are wired to each other so as to make the differences in potential of the second electrode plates common, or the second electrode plates are constructed by one continuous electrode plate.

The present invention is the ion sensor in which conductive polymer films are formed respectively between the first electrode plate and the ion-sensitive film and between the second electrode plate and the ion-sensitive film.

Effect of the Invention

According to the present invention, at the time of making the ion-sensitive film formed on the two electrode plates come into contact with the test solution, according to the difference of thickness of the ion-sensitive film on the two electrode plates, the difference in potential is generated between the two electrode plates. By measuring the difference in potential, the ion concentration in the solution can be measured without any reference electrode and internal solution which are necessary for the ion sensor conventionally.

According to the present invention, the total area of the one or plurality of the openings is not less than the half of the area of the part of the first electrode plate facing the second electrode plate, whereby the area of the part of the ion-sensitive film in the opening of the second electrode plate contacting with the solution is enlarged. Accordingly, the difference in potential between the first electrode plate and the second electrode plate can be increased, whereby the sensor sensitivity which is the ion sensor output about the change of the measured ion concentration.

According to the present invention, the thickness of the ion-sensitive film interposed between the first electrode plate and the second electrode plate is at least not less than the twice of the thickness of the ion-sensitive film formed on the outer surface of the second electrode plate. Accordingly, the difference in potential between the first electrode plate and the second electrode plate can be increased, whereby the sensor sensitivity which is the ion sensor output about the change of the measured ion concentration.

According to the present invention, the plurality of the ion sensors can be mounted by the one sensor support so that the plurality of the sensors can be arranged for each measured ion, whereby various kinds of ion in the solution can be measured simultaneously. By making the second electrode plate common by the wires or by constructing continuously, the wires of each ion sensor can be reduced.

According to the present invention, the conductive polymer film is formed respectively between the first electrode plate and the ion-sensitive film and between the second electrode plate and the ion-sensitive film, whereby the potential between the electrode plates and the ion-sensitive film can be stabilized so that the potential between the electrode plates can be measured with high SN ratio.

DESCRIPTION OF NOTATIONS 1-1 first electrode plate
1-2 first electrode plate
1-3 first electrode plate
2-1 ion-sensitive film
2-2 ion-sensitive film
2-3 ion-sensitive film
3-1 second electrode plate
3-2 second electrode plate
3-3 second electrode plate
4-1 sensor support
4-2 sensor support
5-1 wire
5-2 wire
5-3 wire
5-4 wire
6-1 soldered part
6-2 soldered part 6-3 soldered part
6-4 soldered part
6-5 soldered part
7-1 potentiometer
7-2 potentiometer
7-3 potentiometer
8, 18, 28 opening
9 test solution
9-1 conductive polymer film
9-2 conductive polymer film
10, 20, 30, 40 ion sensor

THE BEST MODE FOR CARRYING OUT THE INVENTION

Explanation will be given on embodiments of the present invention in detail referring to attached drawings.

Members having the same uses and functions are designated by the same reference numerals.

Embodiment 1

Next, explanation will be given on construction of an ion sensor according to a first embodiment of the present invention referring to FIGS. 1 and 2.

Figure 1:
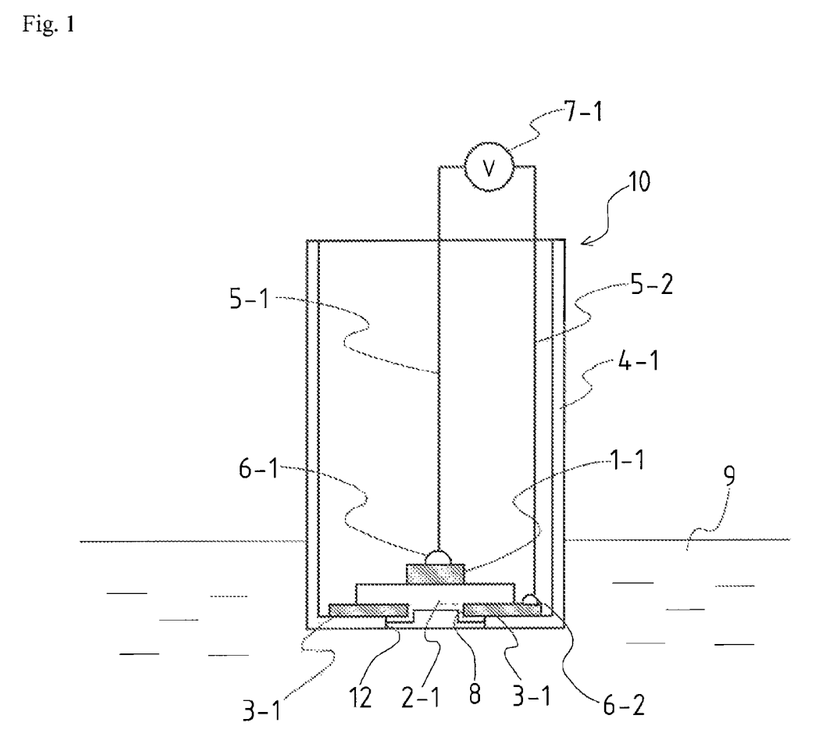
FIG. 1 It is a schematic cross-sectional view of basic structure of an ion sensor which is an embodiment of the present invention.

FIG. 1 is a schematic cross-sectional view of basic structure of an ion sensor which is an embodiment of the present invention. FIG. 2 is a schematic cross-sectional view of structure of the tip of the ion sensor.

An ion sensor 10 detects ion concentration of predetermined ions in a test solution 9 to be examined and mainly has a first electrode plate 1-1, a second electrode plate 3-1, an ion-sensitive film 2-1 and a sensor support 4-1 as shown in FIG. 1.

The first electrode plate 1-1 is a circular platy electrode and is an Ag/AgCl electrode in which a surface of a silver plate is changed into silver chloride.

The second electrode plate 3-1 is a circular plate-like electrode and arranged oppositely to the first electrode plate 1-1. One opening 8 which is a circular through-hole is formed at the center of the second electrode plate 3-1. The second electrode plate 3-1 is an Ag/AgCl electrode in which a surface of a silver plate is changed into silver chloride.

The number and shape of the opening is not limited. For example, it may alternatively be constructed that a plurality of openings are provided or the opening is shaped not circularly, and the opening may be constructed suitably.

The material of the first electrode plate 1-1 and the second electrode plate 3-1 is not limited to Ag/AgCl and may alternatively be platinum, gold or glassy carbon, for example.

The ion-sensitive film 2-1 is a film in which a difference in potential occurs corresponding to measured ion concentration of the test solution 9 at the time of coming into contact with the solution. As shown in FIG. 2, the ion-sensitive film 2-1 is interposed between the first electrode plate 1-1 and the second electrode plate 3-1 and blocks up one of sides of the opening 8 of the second electrode plate 3-1, and extends from the end of that side of the opening 8 to an outer surface 11 of the second electrode plate 3-1 through the inner wall surface of the opening 8 continuously. Thickness t1 of an ion-sensitive film inner layer 2-1(a) which is the ion-sensitive film 2-1 interposed between the first electrode plate 1-1 and the second electrode plate 3-1 is different from thickness t2 of an ion-sensitive film outer layer 2-1(b) which is the ion-sensitive film 2-1 formed on the outer surface 11 of the second electrode plate 3-1. In this embodiment, the thickness t1 of the ion-sensitive film inner layer 2-1(a) is larger than the thickness t2 of the ion-sensitive film outer layer 2-1(b).

The sensor support 4-1 supports the second electrode plate 3-1 so that only the ion-sensitive film 2-1 formed in the opening 8 and on the outer surface 11 of the second electrode plate 3-1 contacts the test solution 9 at the time of measuring ion concentration of the test solution 9. The sensor support 4-1 is cylindrical, and an opening 12 is provided at one of ends of the sensor support 4-1. The sensor support 4-1 enables only the ion-sensitive film outer layer 2-1(b) formed in the opening 8 and on the outer surface 11 of the second electrode plate 3-1 to come into contact with the test solution 9, and is a protector which houses the other parts such as the first electrode plate 1-1 therein and protects them so as not to come into contact with the test solution 9.

The sensor support is not limited to be cylindrical as this embodiment and may alternatively be a sheet-like sensor support, for example.

Next, explanation will be given on manufacture processes of the ion sensor 10 referring to FIGS. 1 and 2.

As shown in FIG. 1, the ion-sensitive film 2-1 of the thickness t1 (the ion-sensitive film inner layer 2-1(a)) is interposed between the first electrode plate 1-1 and the second electrode plate 3-1. A diameter D1 of the first electrode plate 1-1 is set to be 2.5 mm. A diameter of the second electrode plate 3-1 is set to be 6 mm, and a diameter (hole diameter) D2 of the opening 8 is set to be 2.5 mm.

The size and shape of each of the electrode plates are not limited and free shape can be selected suitably under the construction condition under which the function of the ion sensor according to the present invention can be exhibited.

As the ion-sensitive film 2-1, polyvinyl chloride (PVC), dioctyl adipate (DOA) as a plasticizer, and valinomycin which is a potassium ion inductor are mixed and solved into tetrahydrofuran (THF) which is a solvent, and then the mixture is solidified by evaporating the solvent and is employed as a film responding to a potassium ion. As the weight ratio thereof, valinomycin is 2%, PVC is 31% and the solvent is 67%. Naturally, the weight ratio may be changed suitably. Furthermore, tetraphenyl potassium borate or the like as an addition agent may be added so as to change the selectivity about the other ions. The measured ion may be changed from potassium ion to another ion such as sodium, chlorine or calcium by employing a material of ion-sensitive film corresponding to the ion.

Figure 2:
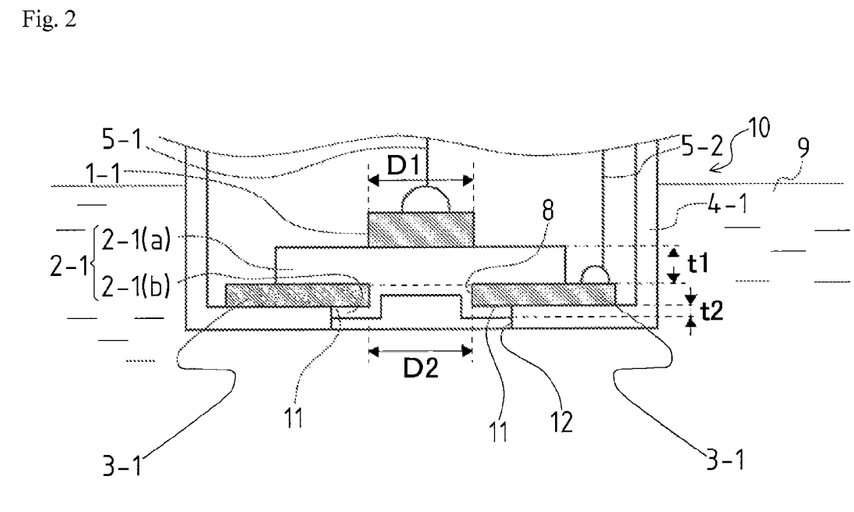
FIG. 2 It is a schematic cross-sectional view of structure of the tip of the ion sensor.

The ion-sensitive film 2-1 for potassium ion is processed to the sectional shape shown in FIG. 2 through several manufacture processes. Concretely, firstly, the ion-sensitive film formed by evaporating THF and whose thickness t1 is 200 μm (the part to be the ion-sensitive film inner layer 2-1(a)) is previously cut off circularly, and a small quantity of THF is added to one of the surfaces of the ion-sensitive film, and then the surface is put on one of sides of the first electrode plate 1-1 and dried up so as to adhere them to each other. Furthermore, the second electrode plate 3-1 having the circular opening 8 is adhered to the other side of the ion-sensitive film (the ion-sensitive film inner layer 2-1(a)) similarly to the method adhering the ion-sensitive film 2-1 to the first electrode plate 1-1. The other side of the second electrode plate 3-1 is adhered to the inner bottom of the sensor support 4-1 which is cylindrical so as to face through the opening 12 of the sensor support 4-1 to the circular opening 8 and the circumference thereof of the second electrode plate 3-1, whereby the part of the second electrode plate 3-1 except for the part to come into contact with the test solution 9 does not face to the outside of the sensor support 4-1. Herein, as the material of the sensor support 4-1, PVC which is the main material of the ion-sensitive film 2-1 is employed. After adhering the second electrode plate 3-1 to the sensor support 4-1, the ion-sensitive film solution at the state solved by THF is dropped to a recess, formed by the ion-sensitive film inner layer 2-1(*a*) exposed through the opening 8 of the second electrode plate 3-1, the inner wall surface of the opening 8, the part on the outer surface 11 of the second electrode plate 3-1 circumferential to the opening 8, and the inner wall surface of the opening 12 of the sensor support 4-1, and is dried up, whereby the ion-sensitive film outer layer 2-1(*b*) which is the part of the ion-sensitive film 2-1 to come into contact with the test solution 9 is formed as shown in FIG. 2. The thickness t2 of the ion-sensitive film outer layer 2-1(*b*) is 13 µm. Though the several processes as mentioned above, the ion-sensitive film 2-1 can be formed which is the ion-sensitive film structure in which the ion-sensitive film inner layer 2-1(*a*) formed by the former processes and the ion-sensitive film outer layer 2-1(*b*) formed by the later processes are continued integrally. Namely, the ion-sensitive film inner layer 2-1(*a*) is interposed between the first electrode plate 1-1 and the second electrode plate 3-1, and the ion-sensitive film inner layer 2-1(*a*) blocks up one of sides of the opening 8 provided in the second electrode plate 3-1, and the ion-sensitive film outer layer 2-1(*b*) is formed continuously from the end of the one side of the opening 8 through the inner wall surface of the opening 8 to the outer surface 11 of the second electrode plate 3-1. According to the construction, at the time of measuring the ion concentration of the test solution 9, the outer surface of the ion-sensitive film outer layer 2-1(*b*) of the ion-sensitive film 2-1 formed in the vicinity of the opening 12 of the sensor support 4-1 comes into contact with the test solution 9.

Wires 5-1 and 5-2 are connected respectively through soldered parts 6-1 and 6-2 to the other side of the first electrode plate 1-1 and one of the ends of the second electrode plate 3-1, and a potentiometer 7-1 is connected between the first electrode plate 1-1 and the second electrode plate 3-1. Accordingly, the difference in potential between the first electrode plate 1-1 and the second electrode plate 3-1 can be measured by the potentiometer 7-1. According to the difference in potential measured by the potentiometer 7-1 (sensor output change), the ion concentration of the potassium ion in the test solution 9 can be measured.

Next, explanation will be given on the principle of action of the ion sensor 10 constructed as mentioned above in detail.

At the time of measuring the ion concentration of the potassium ion in the test solution 9, the ion-sensitive film outer layer 2-1(*b*) formed on the outer surface 11 of the second electrode plate 3-1 which comes into contact with the test solution 9 generates the difference in potential corresponding to the measured ion concentration between the second electrode plate 3-1 and the test solution 9.

On the other hand, since the opening 8 is provided in the second electrode plate 3-1, at the time of measuring the ion concentration, the test solution 9 comes into contact with the ion-sensitive film outer layer 2-1(*b*) formed inside the opening 8, and the test solution 9 faces the first electrode plate 1-1 through the ion-sensitive film outer layer 2-1(*b*) and the ion-sensitive film inner layer 2-1(*a*). Accordingly, the difference in potential of the ion-sensitive film inner layer 2-1(*a*) corresponding to the measured ion concentration in the solution is the difference in potential between the first electrode plate 1-1 and the solution. In this case, the thickness t1 of the ion-sensitive film inner layer 2-1(*a*) interposed between the first electrode plate 1-1 and the second electrode plate 3-1 is different from the thickness t2 of the ion-sensitive film outer layer 2-1(*b*) on the outer surface 11 of the second electrode plate 3-1, and the thickness t1 of the ion-sensitive film inner layer 2-1(*a*) is larger than the thickness t2 of the ion-sensitive film outer layer 2-1(*b*) on the outer surface 11 of the second electrode plate 3-1. According to the difference of thickness of the ion-sensitive film 2-1 on the two electrode plates 1-1 and 3-1, the difference in potential is generated between the two electrode plates 1-1 and 3-1. By measuring the difference in potential (by measuring output change of the ion sensor 10 (mV)), the ion concentration in the solution can be measured. Namely, the ion concentration in the solution can be measured without any reference electrode and internal solution which are necessary for a conventional ion sensor.

(Example of Measurement of Ion Concentration)

Figure 3:
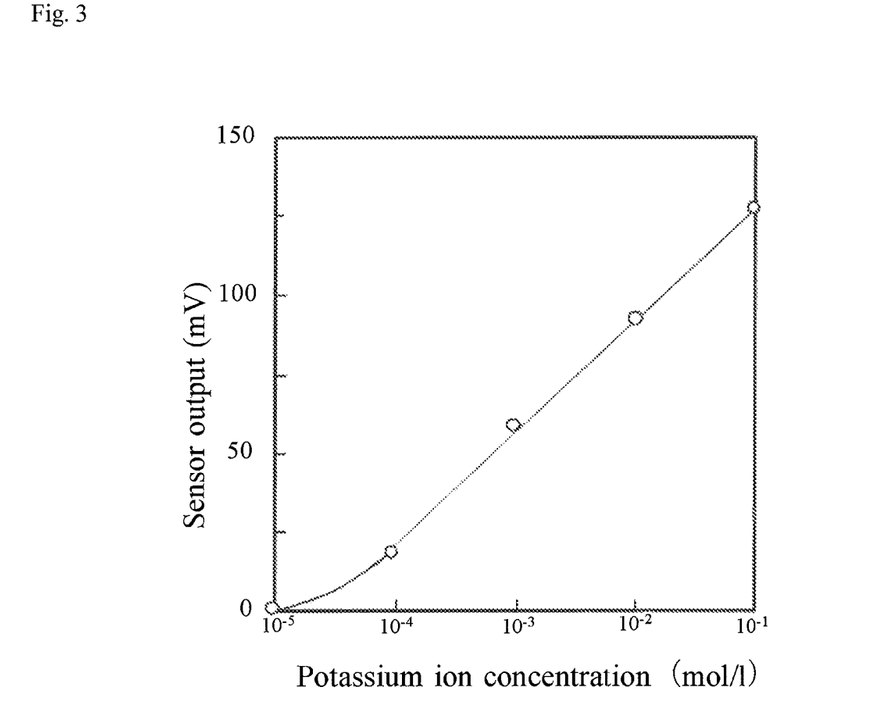
FIG. 3 It is a graph of change of sensor output about change of concentration of potassium ion of the ion sensor.

FIG. 3 shows the sensor output change (mV) with the potassium ion by the ion sensor 10 of the embodiment 1 according to the present invention. As the test solution 9, solutions are employed which is made by solving different concentrations of KCl to tris-boric acid buffer solutions so as to make the potassium ion concentrations within the range between $10^{-5}$ mol/l to $10^{-1}$ mol/l. According to FIG. 3, though the sensitivity is slightly reduced at the concentration of $10^{-5}$ mol/l, the sensitivity is finely linear and 36 mV/decade of the sensor sensitivity is obtained at the potassium ion concentration of not less than $10^{-4}$ mol/l. Accordingly, it is made known that the ion sensor 10 according to the present invention can be employed as an ion sensor without any reference electrode and internal solution.

Embodiment 2

Next, explanation will be given on another embodiment of the ion sensor according to the present invention referring to FIGS. 6 and 7.

Each of the first electrode plate 1-1, the ion-sensitive film 2-1 and the sensor support 4-1 constituting an ion sensor 20 explained in this embodiment is similar to that of the embodiment 1, and explanation thereof is omitted. Only a second electrode plate 3-2 which is another embodiment of the second electrode plate 3-1 of the ion sensor 10 explained in the embodiment 1 will be explained.

Figure 6:
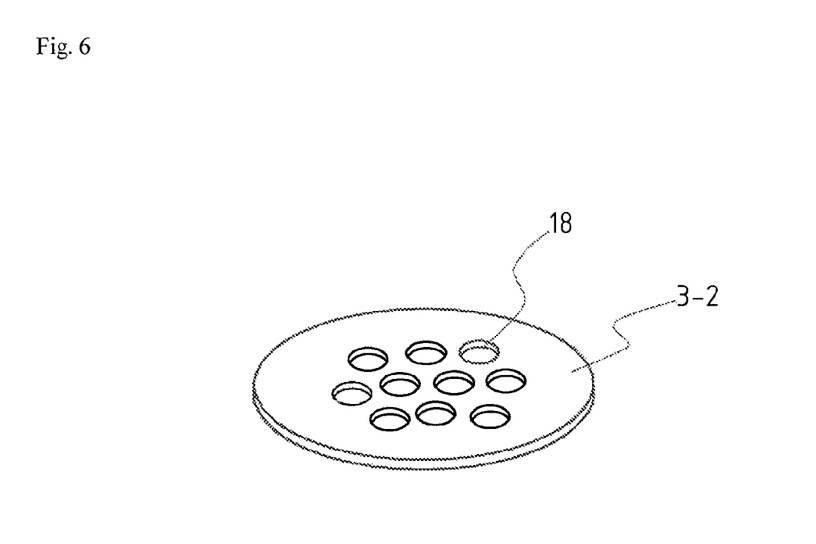
FIG. 6 It is a schematic drawing showing the case that a plurality of openings are provided in the second electrode plate in FIG. 1.
Figure 7:
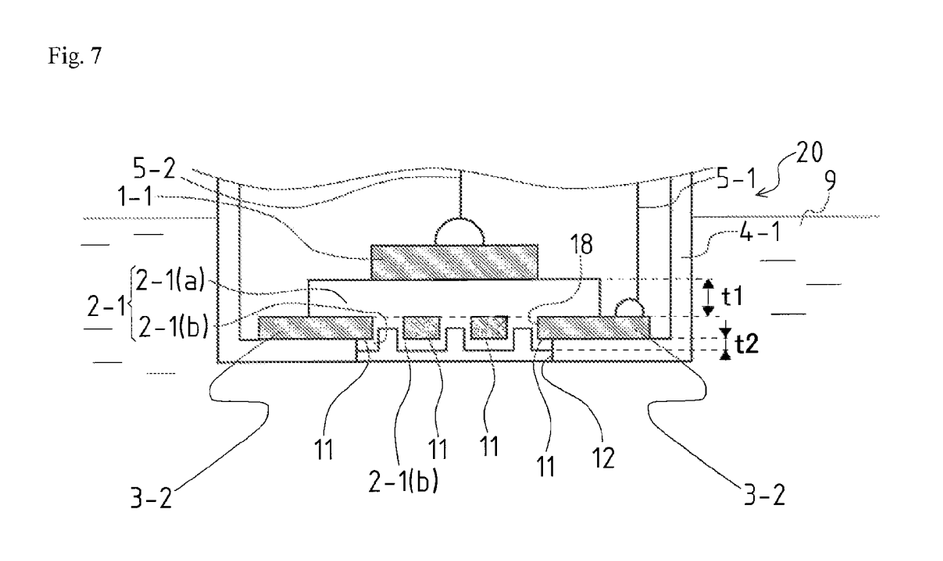
FIG. 7 It is a schematic cross-sectional view of structure of the tip of the ion sensor provided therein with the second electrode plate having a plurality of openings which is a second embodiment of the present invention.

As shown in FIG. 6, the second electrode plate 3-2 is a circular plate-like electrode, has the same outline as the second electrode plate 3-1 in the embodiment 1, and has a plurality of openings 18 which are circular through-holes. The ion sensor 20 shown in FIG. 7 is constructed similarly to the embodiment 1 by employing the second electrode plate 3-2 in which the plurality of the openings 18 are formed instead of the opening 8 explained in the embodiment 1.

By employing the second electrode plate 3-2 in which the plurality of the openings 18 are formed instead of the second electrode plate 3-1 in the embodiment 1 as mentioned above, the lower portion of the ion-sensitive film can be held easily in the case that a flexible ion-sensitive film is interposed between the electrode plates for example, whereby the mechanical intensity of the ion sensor can be improved.

The openings 18 may be a plurality of circles or be lattice-like, and may be shaped suitably.

As mentioned above, the ion sensor 10 (20) includes the first electrode plate 1-1, the second electrode plate 3-1 having the one opening 8 or the second electrode plate 3-2 having the plurality of the openings 18 arranged oppositely to the first electrode plate 1-1, the ion-sensitive film 2-1 interposed between the first electrode plate 1-1 and the second electrode plate 3-1 or the second electrode plate 3-2, blocking up one of sides of the opening 8 (the opening 18) of the second electrode plate 3-1 (3-2), and formed continuously from the end of the side of the opening 8 (the opening 18) through the inner wall surface of the opening 8 (the opening 18) to the outer surface 11 of the second electrode plate 3-1 or the second electrode plate 3-2, and the sensor support 4-1 supporting the second electrode plate 3-1 (3-2) so that only the ion-sensitive film 2-1 formed in the opening 8 (the opening 18) and on the outer surface 11 of the second electrode plate 3-1 (3-2) comes into contact with the test solution 9 at the time of measuring the test solution 9.

The ion sensor 10 (20) measuring the difference in potential between the first electrode plate 1-1 and the second electrode plate 3-1 (3-2) is constructed so that the thickness t1 of the ion-sensitive film inner layer 2-1(*a*) interposed between the first electrode plate 1-1 and the second electrode plate 3-1 is different from the thickness t2 of the ion-sensitive film outer layer 2-1(*b*) formed on the outer surface 11 of the second electrode plate 3-1. Accordingly, when the ion-sensitive film 2-1 formed on the two electrode plates 1-1 and 3-1 (or 1-1 and 3-2) comes into contact with the test solution 9, the difference in potential is generated between the two electrode plates 1-1 and 3-1 (or 1-1 and 3-2) according to the difference of thickness of the ion-sensitive film 2-1 on the two electrode plates 1-1 and 3-1 (or 1-1 and 3-2). Therefore, by measuring the difference in potential, the ion concentration in the solution can be measured without any reference electrode and internal solution which is necessary for a conventional ion sensor. Since any reference electrode and internal solution are not required, the ion sensor can be made small, and the required amount of the test solution is reduced so that a minute sample can be measured easily.

Next, explanation will be given on the method for improving the sensitivity of the ion sensor according to the above embodiment.

Figure 4:
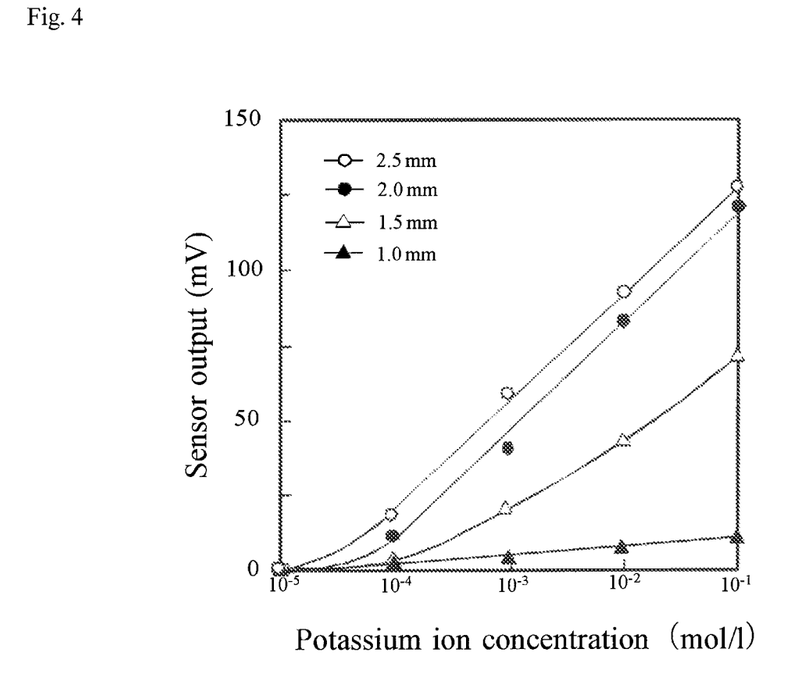
FIG. 4 It is a graph of change of sensor output about change of concentration of potassium ion in the case that a diameter of an opening of a second electrode plate of the ion sensor is changed.

FIG. 4 shows the change of the sensitivity of the ion sensor 10 in the case that the area ratio of the opening 8 of the second electrode plate 3-1 about the area of the first electrode plate 1-1 (the area of the surface facing the second electrode plate 3-1). In the case that a diameter D1 of the first electrode plate 1-1 is 2.5 mm, four sensitivity curves in FIG. 4 correspond respectively to the diameters of the opening 8 shown in FIG. 4 (D2: 1.0 mm, 1.5 mm, 2.0 mm and 2.5 mm). Namely, the second electrode plate 3-1 is made while the maximum and the minimum of the diameter D2 of the opening 8 are respectively 2.5 mm and 1.0 mm, and the second electrode plate 3-1 of each diameter is employed as the second electrode plate of the sensitivity of the ion sensor 10. Then, the test solution 9 of the predetermined potassium ion concentration is measured, and the results are compared. As the measured results, the sensitivity is 36 mV/decade when the diameter D2 is 2.5 mm, and the sensitivity is reduced as the diameter is reduced and the sensitivity is 3 mV/decade when the diameter D2 is 1.0 mm. According to the results, the sensitivity is increased as the area ratio is increased. Namely, it is suitable that the diameter of the opening 8 of the second electrode plate 3-1 is as large as possible. Furthermore, in FIG. 4, the sensitivity of the ion sensor is insufficient when D2 is 1.5 mm (area ratio: 0.36) and the sensitivity of the ion sensor is sufficient when D2 is 2.0 mm (area ratio: 0.64). According to the results, the area of the opening 8 of the second electrode plate 3-1 is preferably larger than the half of the area of the first electrode plate 1-1 (the area of the surface in the first electrode plate 1-1 facing the second electrode plate 3-1).

In the case that a plurality of openings are provided as the openings 18 of the second electrode plate 3-2 in the embodiment 2, the sensitivity is also increased as the area ratio of the openings 18 about the area of the first electrode plate 1-1 is increased. Namely, it is suitable that the diameter of each of the openings 18 of the second electrode plate 3-2 is as large as possible, and the total area of the openings 18 of the second electrode plate 3-2 is preferably larger than the half of the area of the first electrode plate 1-1 (the area of the surface in the first electrode plate 1-1 facing the second electrode plate 3-1).

As mentioned above, the ion sensor 10 (20) is constructed so that the total area of the opening 8 of the second electrode plate 3-1 (the openings 18 of the second electrode plate 3-2) is not less than the half of the area of the part of the first electrode plate 1-1 facing the second electrode plate 3-1 (3-2), whereby the area of the part of the ion-sensitive film 2-1 in the opening 8 (18) of the second electrode plate 3-1 (3-2) contacting with the test solution 9 is enlarged. Accordingly, the difference in potential between the first electrode plate 1-1 and the second electrode plate 3-1 (3-2) can be increased, whereby the sensor sensitivity which is the ion sensor output about the change of the measured ion concentration.

Next, explanation will be given on another method for improving the sensitivity of the ion sensor according to the above embodiment.

Figure 5:
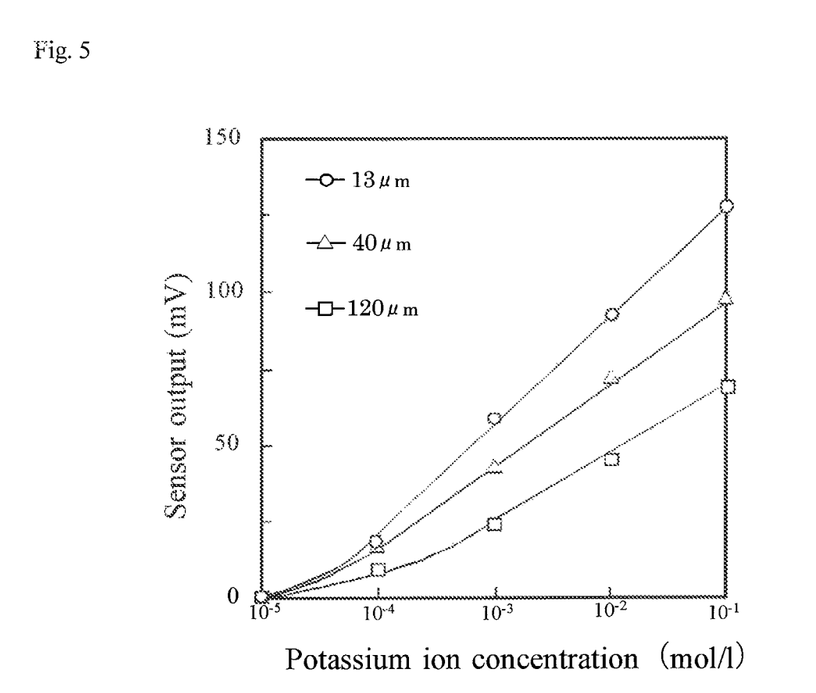
FIG. 5 It is a graph of change of sensor output about change of concentration of potassium ion in the case that thickness of an ion-sensitive film formed on the outer surface of the second electrode plate of the ion sensor is changed.

FIG. 5 shows the change of sensitivity in the case that t1 is fixed and t2 is changed while the thickness of the ion-sensitive film 2-1 interposed between the first electrode plate 1-1 and the second electrode plate 3-1 (the ion-sensitive film inner layer 2-1(*a*)) is regarded as t1 and the thickness of the ion-sensitive film 2-1 formed on the outer surface 11 of the side of the second electrode plate 3-1 coming into contact with the test solution 9 (the ion-sensitive film outer layer 2-1(*b*)) is regarded as t2. In this case, t1 is fixed to 200 μm. The ion sensors having the thickness of 13 μm, 40 μm and 120 μm as t2 are prepared, and the test solution 9 of the predetermined potassium ion concentration is measured and the results are compared. In this case, in the case that a diameter D1 of the first electrode plate 1-1 is 2.5 mm, and the diameter of the second electrode plate 3-1 is 6 mm and the diameter D2 of the opening 8 (opening diameter) is 2.5 mm. As shown in FIG. 5, the sensitivity is 36 mV/decade when t2 is 13 μm, and the sensitivity is reduced as t2 is reduced and the sensitivity is 19 mV/decade when t2 is 120 μm. Accordingly, made known that the sensitivity is increased as t2 is reduced about t1. According to the results, for improving the sensitivity of the ion sensor according to the embodiment, it is conceivable that the thickness t2 of the ion-sensitive film outer layer 2-1(*b*) formed on the outer surface 11 of the side of the second electrode plate 3-1 coming into contact with the test solution 9 is reduced about the thickness t1 of the ion-sensitive film inner layer 2-1(*a*) interposed between the first electrode plate 1-1 and the second electrode plate 3-1. Furthermore, in FIG. 5, the sensitivity of the ion sensor is insufficient when t2 is 120 μm (t1/t2=1.7) and the sensitivity of the ion sensor is sufficient when t2 is 40 μm (t1/t2=5.0). According to the results, the thickness t1 of the ion-sensitive film inner layer 2-1(*a*) interposed between the first electrode plate 1-1 and the second electrode plate 3-1 is preferably at least not less than the twice of the thickness t2 of the ion-sensitive film outer layer 2-1(*b*) formed on the outer surface 11 of the second electrode plate 3-1, that is, it is preferable that the relation t1/t2>2 is satisfied.

As mentioned above, the ion sensor is constructed so that the thickness t1 of the ion-sensitive film inner layer 2-1(*a*) interposed between the first electrode plate 1-1 and the second electrode plate 3-1 is at least not less than the twice of the thickness t2 of the ion-sensitive film outer layer 2-1(*b*) formed on the outer surface 11 of the second electrode plate 3-1. Accordingly, the difference in potential between the first electrode plate 1-1 and the second electrode plate 3-1 can be increased, whereby the sensor sensitivity which is the ion sensor output about the change of the measured ion concentration.

Embodiment 3

Next, explanation will be given on another embodiment of the ion sensor according to the present invention referring to FIG. 8.

Figure 8:
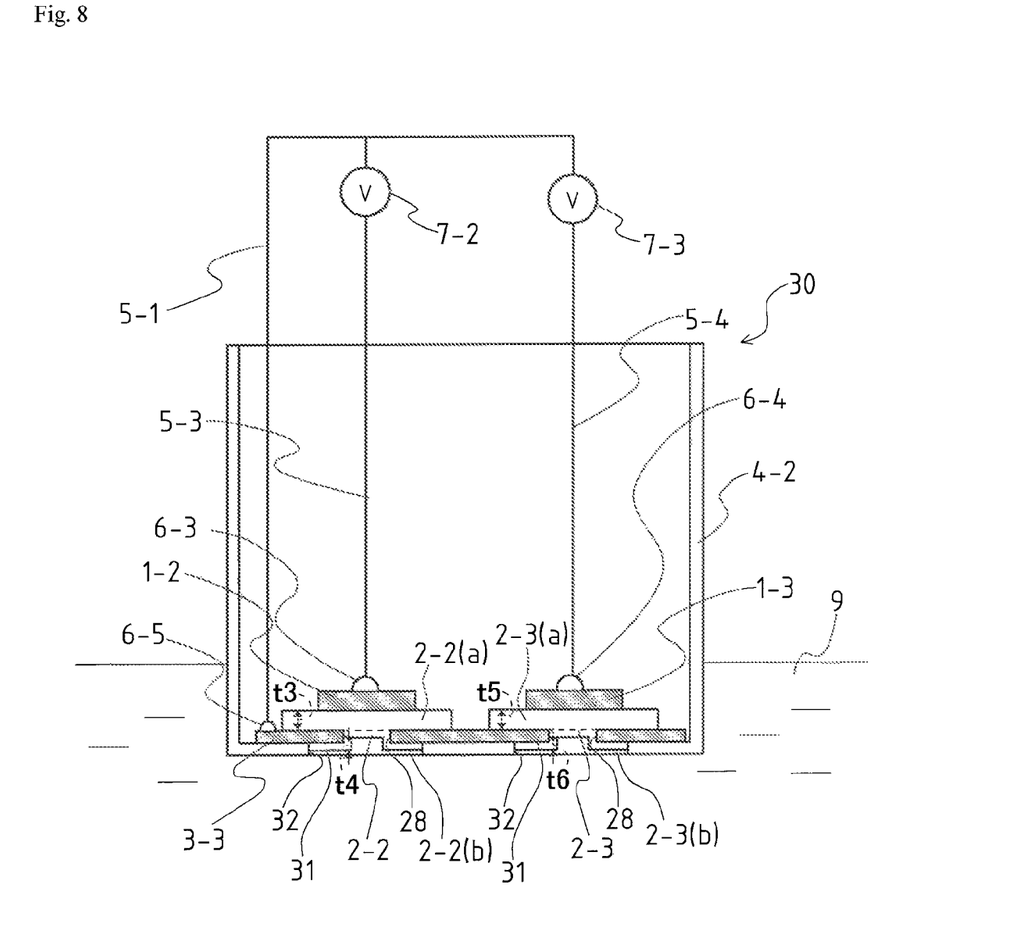
FIG. 8 It is a schematic cross-sectional view of basic structure of the ion sensor constructed by integrating a plurality of ion sensors which is a third embodiment of the present invention.

An ion sensor 30 detects ion concentration of predetermined ions in the test solution 9 to be examined and mainly has first electrode plates 1-2 and 1-3, a second electrode plate 3-3, ion-sensitive films 2-2 and 2-3, and a sensor support 4-2 as shown in FIG. 8.

Each of the first electrode plates 1-2 and 1-3 is a circular platy electrode and is an Ag/AgCl electrode in which a surface of a silver plate is changed into silver chloride.

The second electrode plate 3-3 is a circular plate-like electrode and arranged oppositely to the first electrode plates 1-2 and 1-3, and has two openings 28 each of which is a circular through-hole are formed at predetermined positions. The second electrode plate 3-3 is an Ag/AgCl electrode in which a surface of a silver plate is changed into silver chloride.

The number and shape of the opening is not limited. For example, it may alternatively be constructed that a plurality of openings are provided or the opening is shaped not circularly, and the opening may be constructed suitably.

Each of the ion-sensitive films 2-2 and 2-3 is a film in which a difference in potential occurs corresponding to measured ion concentration of the test solution 9 at the time of coming into contact with the solution. As shown in FIG. 8, the ion-sensitive films 2-2 and 2-3 are interposed between the first electrode plates 1-2 and 1-3 and the second electrode plate 3-3 and block up ones of sides of the openings 28 of the second electrode plate 3-3, and extend from the end of those sides of the openings 28 to an outer surface 31 of the second electrode plate 3-3 through the inner wall surfaces of the openings 28 continuously. Thickness t3 and thickness t5 of ion-sensitive film inner layers 2-2(*a*) and 2-3(*a*) which are the ion-sensitive films 2-2 and 2-3 interposed between the first electrode plates 1-2 and 1-3 and the second electrode plate 3-3 are different respectively from thickness t4 and thickness t6 of ion-sensitive film outer layers 2-2(*b*) and 2-3(*b*) which are the ion-sensitive films 2-2 and 2-3 formed on the outer surface 31 of the second electrode plate 3-3. In this embodiment, the thickness t3 is equal to the thickness t5, and the thickness t4 is equal to the thickness t6. Each of the thickness t3 and the thickness t5 of the ion-sensitive film inner layers 2-2(*a*) and 2-3(*a*) is larger than each of the thickness t4 and the thickness t6 of the ion-sensitive film outer layers 2-2(*b*) and 2-3(*b*).

The sensor support 4-2 supports the second electrode plate 3-3 so that only the ion-sensitive films 2-2 and 2-3 formed in the openings 28 and on the outer surface 31 of the second electrode plate 3-3 contact the test solution 9 at the time of measuring ion concentration of the test solution 9. The sensor support 4-2 is cylindrical, and two openings 32 are provided at one of ends of the sensor support 4-2. The sensor support 4-2 enables only the ion-sensitive film outer layers 2-2(*b*) and 2-3(*b*) formed in the openings 28 and on the outer surface 31 of the second electrode plate 3-3 to come into contact with the test solution 9, and is a protector which houses the other parts such as the first electrode plates 1-2 and 1-3 therein and protects them so as not to come into contact with the test solution 9.

The sensor support is not limited to be cylindrical as this embodiment and may alternatively be a sheet-like sensor support, for example.

Next, explanation will be given on manufacture processes of the ion sensor 30 referring to FIG. 8.

As shown in FIG. 8, the ion sensor 30 is constructed so that two ion sensor elements are integrated in the one sensor support 4-2 (multi ion sensor. Herein, the ion sensor element is a unit of one pair of the first electrode plate, the second electrode plate and the ion-sensitive film). In the ion sensor element shown at the left side in FIG. 8, the ion-sensitive film 2-2 is firmed which responds potassium ion similarly to the embodiment 1. In the ion sensor element shown at the right side in FIG. 8, the ion-sensitive film 2-3 is firmed which responds sodium ion. PVC and DOA which is a plasticizer are employed as the components of the ion-sensitive film 2-3 similarly to the ion-sensitive film 2-2, and bis (12-crown-4) is employed as an ion inductor. As the weight ratio, bis (12-crown-4) is 7%, PVC is 27% and DOA is 66%. The second electrode plate 3-3 is used in common with both sides (the left and right sides shown in FIG. 8) of the ion sensor elements.

Wires 5-3, 5-4 and 5-1 are connected respectively through soldered parts 6-3, 6-4 and 6-5 to the other sides of the first electrode plates 1-2 and 1-3 and one of the ends of the second electrode plate 3-3, and a potentiometer 7-2 is connected between the first electrode plate 1-2 and the second electrode plate 3-3 and a potentiometer 7-3 is connected between the first electrode plate 1-3 and the second electrode plate 3-3. Accordingly, the difference in potential between the first electrode plate 1-2 and the second electrode plate 3-3 and the difference in potential between the first electrode plate 1-3 and the second electrode plate 3-3 can be measured respectively by the potentiometers 7-2 and 7-3. According to the differences in potential measured by the potentiometers 7-2 and 7-3 (sensor output change), the ion sensor 30 can measure the ion concentration of the potassium ion and sodium ion in the test solution 9. By making the second electrode plate 3-3 common to the two ion sensor elements as mentioned above, the number of wires can be reduced. Namely, through two wires are required for one ion sensor, in the case of integrating a plurality of ion sensors, the number of required wires is not the product of 2 and the number of the ion sensors but the sum of 2 and the number of the ion sensors. Accordingly, in the ion sensor 30, the number of wires can be reduced widely in comparison with the case that wires are connected independently to each of ion sensors. In the ion sensor 30, it is not necessary to form each of the ion sensors respectively, whereby the construction can be manufactured easily.

In this embodiment, the second electrode plate is formed integrally by the one continuous second electrode plate 3-3. However, it may alternatively be constructed that second electrode plates are respectively disposed corresponding to a plurality of first electrode plates and the second electrode plates are wired to each other so as to make the differences in potential of the second electrode plates common. In this case, in the entire construction of the ion sensor, the number of wires can be reduced widely.

As mentioned above, the ion sensor 30 is constructed in which the plurality of the ion sensors (ion sensor elements) are disposed on the common sensor support 4-2, and the second electrode plates respectively provided in the ion sensors (ion sensor elements) are wired to each other so as to make the differences in potential of the second electrode plates common, or the second electrode plates are constructed by the one continuous second electrode plate 3-3. Accordingly, the plurality of the ion sensors can be mounted by the one sensor support 4-2 so that the plurality of the sensors can be arranged for each measured ion, whereby various kinds of ion in the solution can be measured simultaneously. By making the second electrode plate common by the wires or by constructing continuously, the wires of each ion sensor can be reduced.

Embodiment 4

Next, explanation will be given on another embodiment of the ion sensor according to the present invention referring to FIG. 9.

Figure 9:
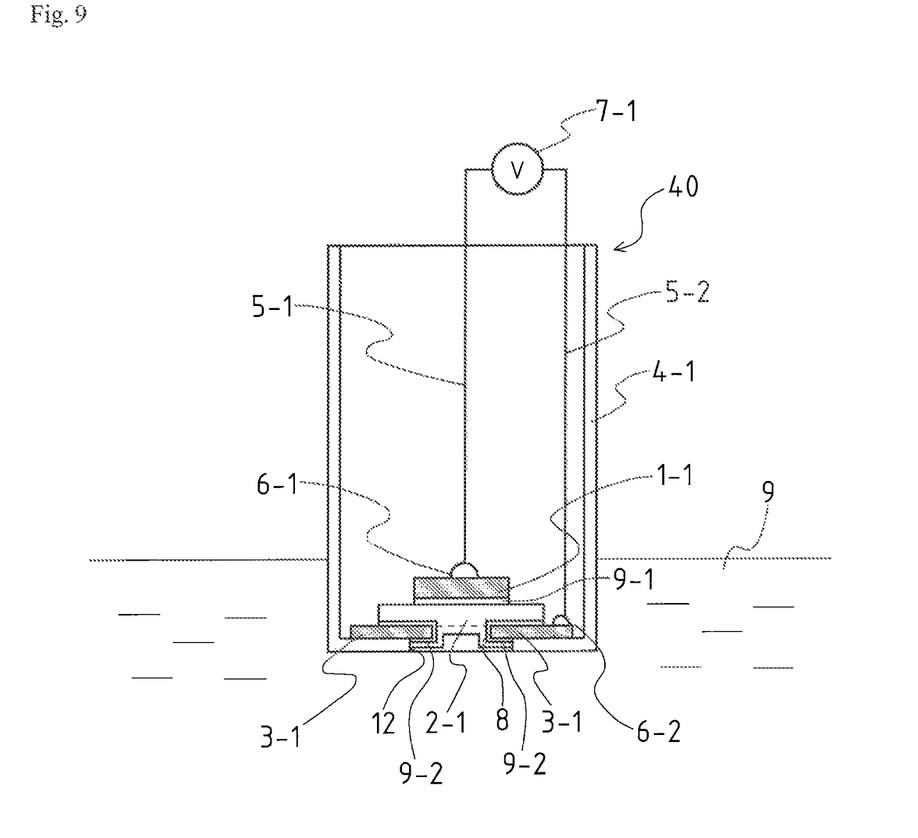
FIG. 9 It is a schematic cross-sectional view of basic structure of the ion sensor in which conductive polymer films are formed between a first electrode plate and the ion-sensitive film and between the second electrode plate and the ion-sensitive film which is a fourth embodiment of the present invention.

FIG. 9 is a schematic cross-sectional view of basic structure of the ion sensor which is a fourth embodiment of the present invention. As shown in FIG. 9, an ion sensor 40 according to this embodiment basically has the same construction as the ion sensor 10 shown in FIG. 1, and explanation of the parts in common with the ion sensor 10 is omitted and a conductive polymer film which differs from the ion sensor 10 will be explained.

In the ion sensor 40, conductive polymer films 9-1 and 9-2 are provided respectively in the interface between the first electrode plate 1-1 and the ion-sensitive film 2-1 and the interface between the second electrode plate 3-1 and the ion-sensitive film 2-1 of the ion sensor 10 according to the embodiment 1. Namely, the conductive polymer film 9-1 is firmed with predetermined thickness between the first electrode plate 1-1 and the ion-sensitive film 2-1 in the ion sensor 10. The conductive polymer film 9-2 is firmed with predetermined thickness between the second electrode plate 3-1 and the ion-sensitive film 2-1 in the ion sensor 10. Herein, the conductive polymer film 9-1 and the conductive polymer film 9-2 have the same components and are formed by material made by the mixture ratio of 1 mL of poly (3,4-ethylenedioxythiophene) and 100 μL of solution of poly (4-styrenesulfonate) of 0.1M. By forming the conductive polymer films 9-1 and 9-2 respectively between the first electrode plate 1-1 and the ion-sensitive film 2-1 and between the second electrode plate 3-1 and the ion-sensitive film 2-1 in the ion sensor 10, the contact potential among the first electrode plate 1-1, the second electrode plate 3-1 and the ion-sensitive film 2-1 can be stabilized, whereby the output of the ion sensor 40 can be stabilized in the long run.

As mentioned above, the ion sensor 40 is constructed so that the conductive polymer films 9-1 and 9-2 are formed respectively between the first electrode plate 1-1 and the ion-sensitive film 2-1 and between the second electrode plate 3-1 and the ion-sensitive film 2-1. Accordingly, the conductive polymer films 9-1 and 9-2 exchange ions for electrons between the first electrode plate and the second electrode plate which are electrode materials and the ion-sensitive film so as to stabilize the contact potential, whereby the potential between the electrode plates and the ion-sensitive film can be stabilized. Therefore, the ion sensor 40 can measure the potential between the electrode plates with high SN ratio.

By employing a sheet-like sensor support instead of the cylindrical sensor support 4-1 or 4-2, the space for mounting the sensor can be reduced.

Accordingly, in the present invention, by employing the ion sensor in which the sensor support is shaped sheet-like, in other words, by forming the sensor support on which the ion sensor is arranged sheet-like, the space for mounting the sensor can be reduced.

Needless to say, the present invention is not limited to the embodiment mentioned above, and the technical range of the present invention includes various changed embodiments and changes of design within the range of the technical thought of the present invention.

INDUSTRIAL APPLICABILITY

The present invention relates to an ion sensor measuring ion concentration in a solution. The invention is used for a conventional clinical hemanalysis device measuring electrolyte concentration in blood and a device measuring ion concentration in a solution of industry or environment. The ion sensor does not require reference electrode, thereby being excellent in miniaturizing and integrating of the sensor. Accordingly, the invention can be used for a micro sensor measuring local ion concentration such as concentration in an organism which is difficult to be measured by a conventional ion sensor.

The invention claimed is:

1. An ion sensor comprising:
   a first electrode plate;
   a second electrode plate arranged oppositely to the first electrode plate and having one or a plurality of openings;
   an ion-sensitive film interposed between the first electrode plate and the second electrode plate, blocking up one of sides of the opening of the second electrode plate, and formed continuously from the end of the side of the opening through the inner wall surface of the opening to the outer surface of the second electrode plate; and
   a sensor support supporting the second electrode plate so that only the ion-sensitive film formed in the opening and on the outer surface of the second electrode plate comes into contact with a test solution at the time of measuring the test solution,
   characterized in that
   difference in potential between the first electrode plate and the second electrode plate is measured while the thickness of the ion-sensitive film interposed between the first electrode plate and the second electrode plate is different from the thickness of the ion-sensitive film formed on the outer surface of the second electrode plate.

2. The ion sensor according to claim 1, wherein the total area of the one or the plurality of the openings of the second electrode is not less than the half of the area of the part of the first electrode plate facing the second electrode plate.

3. The ion sensor according to claim 1, wherein the thickness of the ion-sensitive film interposed between the first electrode plate and the second electrode plate is at least not less than the twice of the thickness of the ion-sensitive film formed on the outer surface of the second electrode plate.

4. An ion sensor characterized in that the plurality of the ion sensors according to claim 3 are disposed on a common sensor support, and the second electrode plates respectively provided in the plurality of the ion sensors are wired to each other so as to make the differences in potential of the second electrode plates common, or the second electrode plates are constructed by one continuous electrode plate.

5. The ion sensor according to claim 1 wherein conductive polymer films are formed respectively between the first electrode plate and the ion-sensitive film and between the second electrode plate and the ion-sensitive film.

6. The ion sensor according to claim 3, wherein conductive polymer films are formed respectively between the first electrode plate and the ion-sensitive film and between the second electrode plate and the ion-sensitive film.

7. An ion sensor characterized in that the plurality of the ion sensors according to claim 1 are disposed on a common sensor support, and the second electrode plates respectively provided in the plurality of the ion sensors are wired to each other so as to make the differences in potential of the second electrode plates common, or the second electrode plates are constructed by one continuous electrode plate.

8. The ion sensor according to claim 7, wherein conductive polymer films are formed respectively between the first electrode plate and the ion-sensitive film and between the second electrode plate and the ion-sensitive film.

* * * * *